US009199226B2

(12) United States Patent
Kauffman et al.

(10) Patent No.: US 9,199,226 B2
(45) Date of Patent: Dec. 1, 2015

(54) ALKANE DEHYDROGENATION CATALYST PERFORMANCE OBTAINED BY A GEL SYNTHESIS METHOD

(71) Applicant: SAUDI BASIC INDUSTRIES CORPORATION, Riyadh (SA)

(72) Inventors: James William Kauffman, Katy, TX (US); Patricia Ann Hooks, Houston, TX (US); Balamurali Krishna Nair, Sugar Land, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/197,308

(22) Filed: Mar. 5, 2014

(65) Prior Publication Data

US 2014/0274672 A1 Sep. 18, 2014

Related U.S. Application Data

(60) Provisional application No. 61/789,249, filed on Mar. 15, 2013.

(51) Int. Cl.
*B01J 21/04* (2006.01)
*B01J 23/02* (2006.01)
(Continued)

(52) U.S. Cl.
CPC .............. *B01J 27/1853* (2013.01); *B01J 27/14* (2013.01); *B01J 27/1856* (2013.01); *B01J 37/036* (2013.01); *C07C 5/48* (2013.01); *B01J 21/04* (2013.01); *B01J 35/026* (2013.01);
(Continued)

(58) Field of Classification Search
CPC ............ B01J 21/04; B01J 23/02; B01J 23/18; B01J 23/40; B01J 37/00; B01J 13/0052; B01J 13/0069
USPC ............ 502/208, 213, 305–355; 516/98, 112, 516/198, 902
IPC ........... B01J 21/04, 23/02, 23/14, 23/18, 23/40, B01J 37/00
See application file for complete search history.

(56) References Cited

U.S. PATENT DOCUMENTS 2,342,247 A * 2/1944 Burk .............................. 502/306
2,932,620 A * 4/1960 Lorenz et al. ................. 502/323
(Continued)

OTHER PUBLICATIONS

International Search Report for International Application No. PCT/US2014/022350; International Filing Date: Mar. 10, 2014; Date of Mailing: Jul. 16, 2014; 4 pages.
Written Opinion of the International Search Report for International Application No. PCT/US2014/022350; International Filing Date: Mar. 10, 2014; Date of Mailing: Jul. 16, 2014; 6 pages.

*Primary Examiner* — Patricia L Hailey
(74) *Attorney, Agent, or Firm* — Cantor Colburn LLP

(57) ABSTRACT

A method of making a catalyst comprises: mixing a catalytically active component and a surfactant to form a mixture, wherein the catalytically active component comprises phosphorus; forming a gel; physically shearing the gel to form a physically sheared gel; combining the physically sheared gel with a support; and calcining the support with the physically sheared gel to form the catalyst. Another method of making a catalyst comprises: mixing a catalytically active component and a surfactant to form a mixture, wherein the catalytically active component comprises phosphorus; letting the mixture sit without mixing for greater than 1 hour to form a set mixture; subjecting the set mixture to shear to form a sheared mixture; combining the sheared mixture with a support; and calcining the support with the sheared mixture to form the catalyst.

20 Claims, 1 Drawing Sheet

(51) Int. Cl.
*B01J 23/18* (2006.01)
*B01J 23/40* (2006.01)
*B01J 37/00* (2006.01)
*B01J 27/185* (2006.01)
*B01J 37/03* (2006.01)
*B01J 27/14* (2006.01)
*C07C 5/48* (2006.01)
*B01J 35/02* (2006.01)

(52) U.S. Cl.
CPC ............ *B01J 37/0009* (2013.01); *B01J 37/038* (2013.01); *B01J 2523/00* (2013.01); *C07C 2521/04* (2013.01); *C07C 2523/02* (2013.01); *C07C 2523/14* (2013.01); *C07C 2527/10* (2013.01); *C07C 2527/14* (2013.01); *C07C 2527/185* (2013.01)

(56) References Cited

U.S. PATENT DOCUMENTS

| 3,789,017 | A | * | 1/1974 | Walker ........................ 502/213 |
| 3,789,078 | A | | 1/1974 | Nolan et al. |
| 4,279,779 | A | * | 7/1981 | Sanchez et al. ............... 502/332 |
| 4,416,804 | A | | 11/1983 | Antos et al. |
| 5,658,497 | A | | 8/1997 | Kumar et al. |
| 5,795,559 | A | * | 8/1998 | Pinnavaia et al. ............. 423/702 |
| 6,414,209 | B1 | | 7/2002 | Herskowitz et al. |
| 6,696,388 | B2 | | 2/2004 | Kourtakis et al. |
| 7,166,470 | B2 | | 1/2007 | Giaquinta et al. |
| 2009/0048097 | A1 | | 2/2009 | Jones et al. |
| 2009/0269266 | A1 | | 10/2009 | Stamires et al. |
| 2012/0088654 | A1 | * | 4/2012 | Wang et al. ................... 502/164 |

* cited by examiner

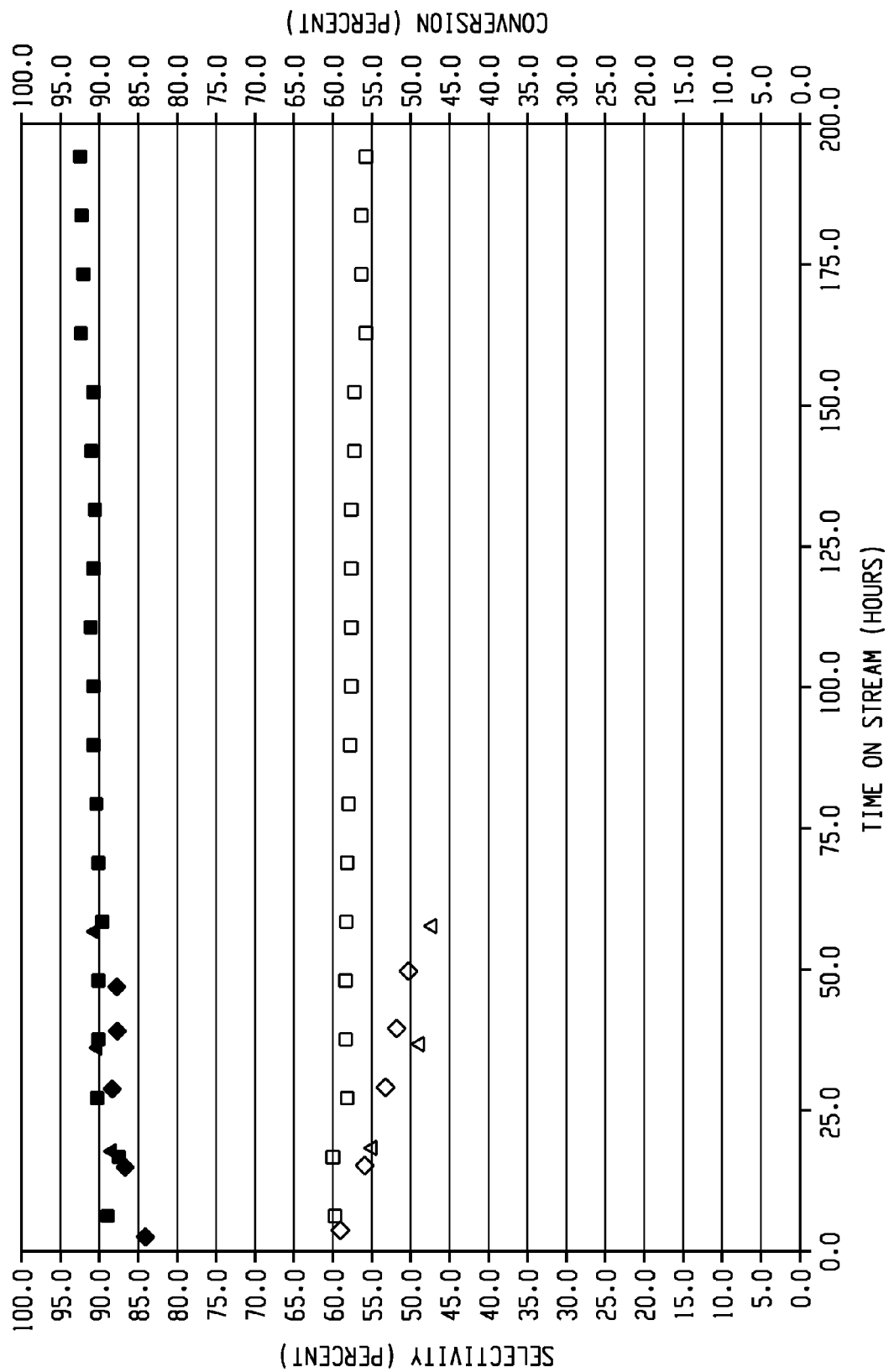

ALKANE DEHYDROGENATION CATALYST PERFORMANCE OBTAINED BY A GEL SYNTHESIS METHOD

CROSS-REFERENCE TO RELATED APPLICATION

This application claims the benefit of U.S. Provisional Patent Application Ser. No. 61/789,249 filed Mar. 15, 2013. The related application is incorporated herein by reference.

TECHNICAL FIELD

The present disclosure relates generally to a method of preparing catalysts for use in alkane dehydrogenation.

BACKGROUND

Paraffins are dehydrogenated to olefins for the manufacture of high octane gasoline, elastomers, detergents, plastics, ion-exchange resins, and pharmaceuticals. The primary cause of catalyst deactivation is the build-up of coke on the catalyst or on the catalyst support surface that leads to the thermal decomposition of the alkane/alkene and eventually inhibits the dehydrogenation reaction.

There is a continuing need to develop new compositions that are more effective catalysts than those currently available in dehydrogenation processes. There is also a need for a catalyst that can be run at higher propane to propylene conversion that produces lower alkane recycle and higher plant throughput and/or that can be operated for longer periods of time during the dehydrogenation cycle between regeneration. Extending the lifetime of the catalyst, would result in a reduction in the amount of overall catalyst and ultimately in the operating costs.

BRIEF SUMMARY

Disclosed herein are methods of making catalysts and catalysts made therefrom.

In an embodiment, a method of making a catalyst comprises: mixing a catalytically active component and a surfactant to form a mixture, wherein the catalytically active component comprises phosphorus; forming a gel; physically shearing the gel to form a physically sheared gel; combining the physically sheared gel with a support; and calcining the support with the physically sheared gel to form the catalyst.

In another embodiment, a method of making a catalyst comprises: mixing a catalytically active component and a surfactant to form a mixture, wherein the catalytically active component comprises phosphorus; letting the mixture sit without mixing for greater than 1 hour to form a set mixture; subjecting the set mixture to shear to form a sheared mixture; combining the sheared mixture with a support; and calcining the support with the sheared mixture to form the catalyst.

These and other features and characteristics are more particularly described below in view of the figures and detailed description.

BRIEF DESCRIPTION OF THE DRAWINGS

For a more complete understanding of the present application, reference is now made to the following descriptions taken in conjunction with the accompanying FIGURE in which:

FIG. 1 is a graphical illustration of selectivity and conversion of the catalyst of Example 1 and the commercial catalyst.

DETAILED DESCRIPTION

The present disclosure relates to a method of making a catalyst for the dehydrogenation of alkanes. The method involves forming a gel from a catalytically active component(s) and a surfactant, shearing the gel, and impregnating the catalytically active component onto a support such as an alumina support by introducing the sheared gel to the support. After impregnation, the catalytically active component can be located on the surface of the support including on the surface of any pores located therein. The catalyst framework of the support can remain free of the catalytically active component. Without being bound by theory, it is believed that the formation of a gel allows for the catalytically active component to remain well distributed throughout the gel by fixing ions in place much like a crystalline matrix. It is possible that adding the well dispersed ions of the catalytically active component to the support, results in an improved ability to remove coke and/or to help to prevent the coke from forming on the surface.

Economic savings from the catalyst of the present disclosure in paraffin conversion, for example, of propane to propylene, can be observed in (i) that the dehydrogenation can be performed at a higher conversion resulting in lower alkane recycle and higher plant throughput and/or (ii) that the catalyst can be used for longer periods of time between regenerations, which would extend the lifetime of the catalyst, thus reducing overall catalyst and operating costs. These economic savings can ultimately be obtained due to the reduced coke build-up on the catalyst. The catalyst made via this technique can therefore achieve excellent lifetime, minimal degradation of conversion, and minimal degradation of selectivity, as compared to a catalyst formed via a method of separate and sequential impregnation of each component in corresponding amounts. In other words, the present catalyst is an improvement over the same catalysts formed via a method of separate and sequential impregnation of each component in corresponding amounts.

The catalyst can be prepared by adding a catalytically active component and a surfactant; mixing the components to form a mixture; and allowing the mixture to form a gel (e.g., allowing the mixture to sit undisturbed until the mixture forms an infinitely connected network, wherein undisturbed refers to allowing the mixture to set without mixing, stirring, or the like). For example, the catalytically active component(s), in the form of nitrates with phosphoric acid can all be mixed together at once with a surfactant. One skilled in the art understands that the gel time is dependent upon the specific components used in the mixture. The gel point can be easily determined for a given mixture using a typical tube inversion method or by rheological techniques. For example, the gel time can be greater than 0.5 hours (hr), specifically, greater than or equal to 1 hour, and more specifically, greater than or equal to 2 hours, greater than or equal to 5 hours, and even greater than or equal to 8 hours. For example, the gel time can be 0.5 to 48 hr, or 1 to 24 hr, or 2 to 12 hr, or 1 to 8 hr. It is noted that although the formation of the gel can be accomplished in under 8 hr, the mixture can be allowed to set beyond the time needed for gel formation.

After formation of the gel, the gel can be prepared for combination with the support. Optionally, physical shearing can be applied to the gel to liquefy the gel. In other words, shear can be employed to break bonds in the gel, enabling the gel to flow. The gel can then be disposed on the support, e.g., can be impregnated onto the support, for example, into the pores of the support. Optionally, additional catalytically active component(s) can be deposited onto the support material before or after the sheared gel is added to the support and/or additional catalytically active components can be added to the sheared gel before impregnation onto the support.

The support with the gel can then be dried and/or calcined to remove water and other volatile materials to form the catalyst. The drying can occur at room temperature or at an elevated temperature of 25 to 500 degrees Celsius (° C.), more specifically, 120 to 200° C., e.g., for a period of time sufficient to dry the impregnated support. The drying time can be 0.5 to 10 hr, specifically, 0.5 to 5 hr. The calcining can occur at a temperature of 200 to 1,000° C., specifically, 500 to 800° C., more specifically, 550 to 700° C., e.g., for a period of time sufficient for calcination. The calcination can be for 1 to 20 hr, specifically, 5 to 15 hr, and more specifically, 8 to 12 hr. Any commercial calciner can be used, such as fixed bed or rotating calciners. Calcination can be performed in various atmospheres such as in air, oxygen, inert atmosphere (e.g., nitrogen), steam, or mixtures thereof. The total preparation time of the catalyst can be, for example, 2.5 to 54 hr.

The support can optionally be formed prior to impregnation of the catalytically active component. For example, the support can be formed into 1/16 inch (1.6 millimeters (mm)) to 1/2 inch (12.7 mm) pellets by compression molding, extrusion, or simply screened to a desired mesh size such as a 10-28 mesh and calcined prior to impregnating the support with the gel.

The catalytically active component(s) is dependent upon the reaction that the catalyst is intended to catalyze, e.g., based upon various combinations of elements from Groups 1 to 17 of the periodic table of elements. For example, the catalytically active component(s) can comprise titanium, zirconium, cerium, lanthanum, aluminum, chromium, phosphorus, and iron, as well as combinations comprising at least one of the foregoing components.

The catalytically active component can comprise phosphorus and the gel network can be a phosphorus-based network. The phosphorus component can be added as an acid such as phosphoric acid, hypophosphorous acid, phosphorous acid, peroxomonophosphoric acid, hypophosphoric acid, pyrophosphoric acid, triphosphoric acid, and the like, as well as combinations comprising at least one of the foregoing. The phosphorus component can comprise phosphoric acid. The phosphorus component can be present in an amount of 0.5 to 4 weight percent (wt %), specifically, 0.7 to 3 wt %, and more specifically, 0.8 to 1.5 wt %, based upon a total weight of the mixture.

In addition to phosphorus, the catalytically active component(s) can comprise elements from Groups 2, 10, 14, or a combination comprising one or more of the foregoing. For example, the catalytically active component(s) can comprise the platinum, tin, nickel, and calcium. Generally, negative components such as nickel, phosphorus, and calcium are a problem in alkane dehydrogenation as they are believed to increase coking. However, it was unexpectedly discovered that nickel, phosphorus, and calcium could be successfully used for alkane dehydrogenation due to the improved properties of the present catalyst (e.g., resistance to coking and/or facile decoking).

The concentration of the catalytically active component(s) can vary widely, for example, from 0.01 to 10 molar or more, depending on the solubility of the particular materials employed. For example, based upon a total weight of the mixture the mixture can comprise at least one of the following components: 0.2 to 2 wt % platinum, specifically, 0.5 to 1.5 wt % platinum, and more specifically, 0.7 to 1.2 wt % platinum; 0.2 to 5 wt % tin, specifically, 1 to 4 wt % tin, and more specifically, 2 to 3.5 wt % tin; 0.1 to 4 wt % nickel, specifically, 0.5 to 2.5 wt % nickel, and more specifically, 0.8 to 1.5 wt % nickel; 0.1 to 5 wt % calcium, specifically, 1 to 5 wt % calcium, and more specifically, 1.2 to 2.0 wt % calcium.

The catalytically active component can be added to the mixture in any form that is water soluble. For example, the catalytically active component can be added as one or more of a metal salt, such as nitrate, ammonium, or chloride salts; salts of organic acids, carbonates, or oxides; or a combination comprising one or more of the foregoing. Optionally, the salt can be a hydrated salt.

The pH of the catalytically active component can be adjusted by addition of an acid, such as hydrochloric acid, nitric acid, sulfuric acid, acetic acid, oxalic acid, and formic acid, or a base such as sodium hydroxide, ammonium hydroxide, potassium hydroxide, sodium bicarbonate, and potassium bicarbonate. The pH can be 1 to 6, specifically, 2 to 5, more specifically, 3 to 4.

A surfactant can be used, e.g., to help prevent agglomeration and/or to facilitate gel formation. The surfactant can be any surfactant such as an alkyl sulfate, an alkyl sulfonate, an alkyl phosphate, an alkyl carboxylate, a polyoxyproplyene glycol alkyl ether, a glucoside alkyl ether, a polyoxyethylene glycol octylphenol ether, a polyoxyethylene glycol alkylphenol ether, a polyoxyethylene glycol alkyl ether, a glycerol alkyl ester, a polyoxyethylene glycol sorbitan alkyl ester, a polysorbate, a block copolymer of polyethylene glycol and polypropylene glycol, and the like, as well as combinations comprising at least one of the foregoing surfactants. The surfactant can comprise a $C_{6-16}$ alkyl sulfonate, such as dodecylbenzenesulfonic acid. Specific examples of surfactants include perfluorononanoate, perfluorooctanoate, octenidine dihydrochloride, cetyl trimethylammonium bromide, cetyl trimethyl ammonium chloride, cetylpyridinium chloride, benzethonium chloride, dimethyldioctadecylammonium chloride, dioctadecyldimethylammonium bromide, sodium stearate, sodium lauroyl sarcosinate, 3-[(3-cholamidopropyl)dimethylammonio]-1-propanesulfonate, cocamidopropyl hydroxysultaine, cetyl alcohol, cetostearyl alcohol, oleyl alcohol, cocamide monoethanolamine, cocamide diethanolamine, dodecyldimethylamine oxide, and polyethoxylated tallow amine. The mixture can be free of a sulfated surfactant, e.g., there is no added sulfated surfactant.

The surfactant can be present in the amount of 0.01 to 1 wt %, specifically, 0.05 to 0.5 wt %, more specifically, 0.08 to 0.2 wt %, based upon a total weight of the mixture.

The support can comprise a heat-resistant oxide or a mixed oxide. The oxide can comprise one or more of zirconium dioxide, zinc oxide, aluminum oxide, silicon dioxide, titanium dioxide, magnesium oxide, lanthanum oxide, cerium oxide, and the like. The support can, for example, be a large pore support, e.g. having an average pore diameter range of greater than or equal to 90 angstroms (Å), for example, 90 to 250 angstroms (Å). Alternatively, or in addition, the support can have a large average surface area, e.g., greater than or equal to 50 meter squared per gram ($m^2/g$), such as, 50 to 150 $m^2/g$. The support can be a calcined support. Prior to forming the catalyst, the support can be treated with, for example, the sources of the various materials described above.

The support can comprise an alumina support. The alumina support can be any form of crystalline alumina material, such as η-alumina, θ-alumina, χ-alumina, γ-alumina materials, or a combination comprising one or more of the foregoing. Those having a large surface area can be particularly useful, where the alumina support can have a surface area of 50 to 150 m²/g and a pore diameter range of 90 to 250 angstroms to obtain a desired pore size distribution. The alumina support can be thermally stabilized by calcining prior to or during the formation of the final catalyst.

The support can be an extrudate that can be obtained from a catalyst manufacturer or can be made by preparing a precursor, forming it into the desired catalyst shape, and calcining the precursor to give the final support. The support can be configured in various shapes and sizes. For example, the shape and size can be cylindrical in shape with a ⅛ inch (1.6 mm) diameter that can vary in length, such as ⅛ inch (1.6 mm) or less to up to several inches. In certain applications, the shape and size can be spherical or tablet-shaped or configured into other shapes, such as a star shape, where the thickness of the particle can be of various thicknesses, which can be greater than or less than ⅛ inch (3.1 mm) thick (e.g., 1/16 inch (1.6 mm) to ½ inch (12.7 mm)) The support can be calcined prior to incorporation of the catalytically active component to ensure it has the proper surface area and pore structure and crystalline phase. The support can be dried (e.g., at 120° C. for 2 hr) before the impregnation if desired.

The final catalyst can comprise the catalytically active component(s) in an amount of 0.1 to 15 wt %, specifically, 3 to 10 wt %, and more specifically, 5 to 8 wt %, based upon a total weight of the final catalyst (i.e., after drying and calcination). For example, the final catalyst can comprise at least one of the following: 0.1 to 20 wt % phosphorus, 0.1 to 75 wt % tin, and 0.1 to 10 wt % of Group 1 and/or 2 metals, based upon a total weight of the catalytically active component(s).

The catalyst can be used in a dehydrogenation process, including oxidative dehydrogenation, and can be used to convert hydrocarbons such as paraffin and/or alkane hydrocarbons into the corresponding olefins. The conversion conditions can be those dehydrogenation reaction conditions useful to form dehydrogenated hydrocarbon products, such as a propane feed that is dehydrogenated to form propylene. The process can be carried out by forming a mixture, preferably preheated, of hydrocarbon feed, steam, if used, and oxygen and/or oxygen-containing gases, if used, and passing this mixture over the catalyst at the desired temperature. A steam or water co-feed can be used in the reaction with the hydrocarbon feed. The steam or water can act as a carrier gas to facilitate introduction of the hydrocarbon into the reactor. The steam can act to carry heat into the reactor since the dehydrogenation is an endothermic reaction and can act to minimize coking, for example, by at least partially removing coke and/or by inhibiting coke formation on the catalyst. The steam can also serve to dilute the hydrocarbon feed so the catalyst is not quickly coked and the reactor is not cooled too much due to the endothermic dehydrogenation reaction. Steam can also serve as a diluent that can shift the equilibrium conversion to higher values. In certain applications, the hydrocarbon/water molar feed ratio can be 1:1 to 10:1, specifically, 1:2 to 1:6, and more specifically, 1:3 to 1:5. The molar ratio of water vapor to the paraffin hydrocarbons can be 0.5:1 to 10:1, specifically, to 1:1 to 6:1. The catalyst can be used with feed materials that contain hydrocarbons of the group comprising $C_{2-6}$ paraffins.

The hydrocarbon feed stream can optionally be mixed with steam and put into contact with the present catalyst at a temperature of 300 to 750° C., and a pressure of 0.01 to 17 bar (absolute), specifically, 1 to 5 bar (absolute). Recycle of unconverted organic compound feed can be employed if desired; however, the conversion rates and selectivity of this disclosure are generally sufficiently high to justify a single pass operation, if, for example, the product streams can be used without separation steps in a subsequent operation, such as polymerization.

The dehydrogenation reaction can be a non-oxidative dehydrogenation reaction wherein the reaction is carried out in an oxygen-free or substantially oxygen-free (i.e. no oxygen gas or $O_2$) environment. Furthermore, the reaction can be carried out without any hydrogen gas ($H_2$) co-feed, as is used in some dehydrogenation reactions. Any diluents, which can be inert diluents such as helium, can also be used in the reaction.

The feed streams can be preheated and introduced into the reactor at a temperature of 200 to 300° C. The hydrocarbon, steam and diluent feed can be introduced into the reactor at a gas hourly space velocity (GHSV) of 2,100 to 4,500 $hr^{-1}$, more specifically, 3,000 to 3,500 $hr^{-1}$.

Because the dehydrogenation reaction is endothermic, heat input can be required to maintain the reaction. The dehydrogenation reaction can be carried out in a tube-type fixed bed reactor that is provided with a heat source to maintain suitable reaction temperatures. Other suitable reactors can be used however. The reaction temperature can be 525 to 610° C., specifically, 545 to 595° C. If a higher purity propylene is desired then the product stream can be processed through a purification unit.

Set forth below are examples of the method and catalyst disclosed herein.

Embodiment 1

A method of making a catalyst, comprising: mixing a catalytically active component and a surfactant to form a mixture, wherein the catalytically active component comprises phosphorus; forming a gel; physically shearing the gel to form a physically sheared gel; combining the physically sheared gel with a support; and calcining the support with the physically sheared gel to form the catalyst.

Embodiment 2

A method of making a catalyst, comprising: mixing a catalytically active component and a surfactant to form a mixture, wherein the catalytically active component comprises phosphorus; letting the mixture sit without mixing for greater than 1 hour to form a set mixture; subjecting the set mixture to shear to form a sheared mixture; combining the sheared mixture with a support; and calcining the support with the sheared mixture to form the catalyst.

Embodiment 3

The method of Embodiment 2, wherein the mixture sits until a gel forms.

Embodiment 4

The method of any of Embodiments 1-3, wherein the mixture sits for greater than 1 hour without mixing.

Embodiment 5

The method of any of Embodiments 1-4, wherein the catalytically active component comprises one or more elements from one or more of Groups 2, 10, 14, and 15.

Embodiment 6

The method of any of Embodiments 1-5, wherein the catalytically active component comprises platinum, tin, nickel, phosphorus, calcium, or a combination comprising at least one of the foregoing.

Embodiment 7

The method of any of Embodiments 1-6, wherein the support comprises a calcined alumina support.

Embodiment 8

The method of any of Embodiments 1-7, wherein the total preparation time of the catalyst is 2.5 to 54 hours.

Embodiment 9

The method of any of Embodiments 1-8, wherein the catalyst comprises 0.1 to 20 wt % phosphorus, 0.1 to 75 wt % tin, and 0.1 to 10 wt % of Group 1 and/or 2 metals, based upon a total weight of the catalytically active component(s)

Embodiment 10

The method of any of Embodiments 1-9, wherein the catalyst comprises 0.2 to 25 wt % platinum, 0.2 to 5 wt % tin, 1 to 3 wt % phosphorus, 0.1 to 5 wt % calcium, 0.1 to 2 wt % chlorine, and 0.1 to 4 wt % nickel, based upon a total weight of the catalyst.

Embodiment 11

The method of any of Embodiments 1-10, wherein the catalyst comprises 0.5 to 1.5 wt % platinum, 1 to 4 wt % tin, 1 to 2 wt % phosphorus; 1 to 5 wt % calcium, 0.12 to 1 wt % chlorine, 0.5 to 2.5 wt % nickel, based upon a total weight of the catalyst.

Embodiment 12

The method of any of Embodiments 1-11, wherein the catalyst comprises 0.7 to 1.2 wt % platinum, 2 to 3.5 wt % tin, 1.1 to 1.5 wt % phosphorus, 1.2 to 2.0 wt % calcium, 0.12 to 0.6 wt % chlorine, 0.8 to 1.5 wt % nickel, based upon a total weight of the catalyst.

Embodiment 13

The method of any of Embodiments 1-12, wherein mixture can be free of a sulfated surfactant.

Embodiment 14

The method of any of Embodiments 1-13, wherein the mixture sits for greater than or equal to 2 hours without mixing.

Embodiment 15

The method of any of Embodiments 1-14, wherein the mixture sits for greater than or equal to 5 hours without mixing.

Embodiment 16

The method of any of Embodiments 1-15, wherein the mixture sits for greater than or equal to 8 hours without mixing.

Embodiment 17

A catalyst formed by the method of any of Embodiments 1-16.

Embodiment 18

The catalyst of Embodiment 17, wherein the catalyst has a percent conversion of alkanes of greater than or equal to 50% for greater than or equal to 75 hours.

Embodiment 19

The catalyst of any of Embodiments 17-18, wherein the catalyst has a percent conversion of alkanes of greater than or equal to 55% for greater than or equal to 150 hours.

Embodiment 20

The catalyst of any of Embodiments 17-19, wherein the alkane dehydrogenation is the reaction of propane to propylene.

The following examples are provided to illustrate the method of preparing the catalyst of the present disclosure. The examples are merely illustrative and are not intended to limit methods made in accordance with the disclosure to the materials, conditions, or process parameters set forth therein.

EXAMPLES

Example 1

Catalyst Preparation

An aqueous mixture was formed from the components listed in Table 1, where the amounts are listed in either grams (g) or milliliters (mL), to form a 1 wt % phosphorus mixture with a Ca:Ni:P ratio of 0.9:0.1:1.

TABLE 1

| Component | Amount added |
|---|---|
| $H_3PO_4$ | 0.84 g |
| HCl | 0.2 mL |
| Water | 3.95 mL |
| Triton X-100 | 2 drops |
| $Ni(NO_3)_2 \cdot 6H_2O$ | 0.20 g |
| $SnCl_2 \cdot 2H_2O$ | 0.62 g |
| $Ca(NO_3)_2 \cdot 4H_2O$ | 1.56 g |
| $H_2PtCl_6$, aqueous, 20% Pt | 0.5 mL |

The mixture was allowed to sit for 16 hr until a gel was formed. The gel was then physically sheared with a spatula to break apart the gel. The physically sheared gel was impregnated onto 14 g of a calcined alumina support, SCl eta-alumina, (commercially available from Sud-Chemie Inc., Louisville, Ky.) and calcined at 500° C. in air for 2 hr, to form the catalyst. The catalyst was cooled to room temperature and stored in dry nitrogen.

Example 2

Dehydrogenation of Propane to Propylene

Two dehydrogenation reactions of propane to propylene were performed using the catalyst of Example 1 and a commercially available catalyst. The commercially available catalyst, was a platinum on alumina propane dehydrogenation catalyst that is widely commercially used for dehydrogenation reactions.

The time-on-stream was eight hours with a one hour regeneration period. The concentration of $O_2$ used was 2.8 mole % with a flow of 20 standard cubic centimeters per minute (sccm). There was always a 5° C. temperature difference between set temperature of the furnace and the bed thermocouple during $N_2$ purge cycles. During other cycles (dehydrogenation and regeneration) this difference is dictated by the endothermicity or exothermicity of the reaction in addition to the above. The set point was kept at 550° C. for the dehydrogenation and reduced to 485° C. for the regeneration. The changes in the temperature profile were made at the start of the purge cycle (with $N_2$) just before the dehydrogenation and regeneration respectively. This ensured the temperatures were at a steady state before the start of dehydrogenation and regeneration.

FIG. 1 shows the conversion and selectivity data for dehydrogenation reaction of both the catalyst of Example 1 (squares) and the commercial catalyst (diamond/triangle), where each data point represents a seven hour dehydrogenation period (as set forth above) and a regeneration period. Although both catalysts exhibited a selectivity of greater than 90%, it is clear from the graph that at the same catalyst loading, with the same process conditions, that the catalyst of Example 1 (open squares) shows very little decrease in conversion with time as compared to the commercial catalyst (open diamonds and triangles). Not to be limited by theory, but it is believed that this decrease in conversion with time of the commercial catalyst is attributed to the build-up of coke on the commercial catalyst that covers the platinum particles and preventing the dehydrogenation reaction from occurring. It is to be noted that the equilibrium conversion line i.e., the theoretical limit to conversion, is at 70%, and hence, the conversion of the present catalyst is high.

The catalyst of Example 1 does not show a decline in conversion indicating that there was no appreciable coke build-up on the catalyst surface. It should further be noted that the reactions were run at the high temperature of 595° C. in order to accelerate any coking that would otherwise occur on the catalyst and still the catalyst of Example 1 was able to resist coke build-up. While it is expected that the lifetime of the catalyst will further increase at lower operating temperatures, the ability of the catalyst of Example 1 to operate at higher temperatures advantageously allows for a higher conversion to propylene.

The relatively rapid decrease in conversion for the commercial catalyst versus the gel treated catalyst indicates that coke is forming much faster on the commercial catalyst and is covering up the platinum sites, thus leading to lower conversion. Interestingly, the commercial catalyst decreases to a 55% conversion in about 16 hr whereas, it takes the catalyst formed by impregnating with the gel more than 10 times longer to decrease to the same conversion showing a significant improvement in inhibiting coke formation.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The endpoints of all ranges directed to the same component or property are inclusive of the endpoint and independently combinable. "Or" means "and/or" unless the context specifies otherwise.

Disclosure of a narrower range in addition to a broader range is not a disclaimer of the broader range.

Unless otherwise defined, all terms (including technical and scientific terms) used herein have the same meaning as commonly understood by one of ordinary skill in the art to which this disclosure belongs.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between 1 and 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

As used herein, catalytic activity can be expressed as the % moles of the hydrocarbon or reactant converted with respect to the moles of hydrocarbon or reactant fed. In propane dehydrogenation where propane is converted to propylene, the catalytic activity can be measured by the propane converted with respect to the moles of propane fed and can be defined by the following formulas:

$$\text{Mole \% Propane Conversion} = [(T_i - T_o)/T_i] \times 100 \quad (1)$$

where, $T_i$, is the number of moles of propane fed and $T_o$ is the number of moles propane unreacted. As used herein, selectivity for propylene can be expressed as:

$$\text{Mole \% Propylene Selectivity} = [X_t/(T_i - T_o)] \times 100 \quad (2)$$

where, $X_t$, is the number of moles of total propylene in the product.

While the disclosure has been described with reference to an exemplary embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A method of making a catalyst, comprising:
   mixing a catalytically active component and a surfactant to form a mixture, wherein the catalytically active component comprises phosphorus;
   forming a gel;
   physically shearing the gel to form a physically sheared gel;
   combining the physically sheared gel with a support; and
   calcining the support with the physically sheared gel to form the catalyst.

2. The method of claim 1, wherein the forming comprises letting the mixture sit for greater than 1 hour without mixing.

3. The method of claim 1, wherein the catalytically active component comprises one or more elements from one or more of Groups 2, 10, 14, and 15.

4. The method of claim 1, wherein the catalytically active component comprises platinum, tin, nickel, phosphorus, calcium, or a combination comprising at least one of the foregoing.

5. The method of claim 1, wherein the support comprises a calcined alumina support.

6. The method of claim 1, wherein the total preparation time of the catalyst is 2.5 to 54 hours.

7. The method of claim 1, wherein the catalyst comprises 0.1 to 20 wt % phosphorus, 0.1 to 75 wt % tin, and 0.1 to 10 wt % of Group 1 and/or 2 metals, based upon a total weight of the catalytically active component.

8. The method of claim 1, wherein the catalyst comprises 0.2 to 25 wt % platinum, 0.2 to 5 wt % tin, 1 to 3 wt % phosphorus, 0.1 to 5 wt % calcium, 0.1 to 2 wt % chlorine, and 0.1 to 4 wt % nickel, based upon a total weight of the catalyst.

9. The method of claim 1, wherein the catalyst comprises 0.5 to 1.5 wt % platinum, 1 to 4 wt % tin, 1 to 2 wt % phosphorus; 1 to 5 wt % calcium, 0.12 to 1 wt % chlorine, 0.5 to 2.5 wt % nickel, based upon a total weight of the catalyst.

10. The method of claim 1, wherein the catalyst comprises 0.7 to 1.2 wt % platinum, 2 to 3.5 wt % tin, 1.1 to 1.5 wt % phosphorus, 1.2 to 2.0 wt % calcium, 0.12 to 0.6 wt % chlorine, 0.8 to 1.5 wt % nickel, based upon a total weight of the catalyst.

11. The method of claim 1, wherein mixture can be free of a sulfated surfactant.

12. The method of claim 1, wherein the mixture sits for greater than or equal to 2 hours without mixing.

13. The method of claim 1, wherein the mixture sits for greater than or equal to 5 hours without mixing.

14. The method of claim 1, wherein the mixture sits for greater than or equal to 8 hours without mixing.

15. The method of claim 1, wherein the catalytically active component comprises platinum, tin, nickel, phosphorus, calcium, or a combination comprising at least one of the foregoing.

16. A catalyst formed by the method of claim 1.

17. A method of making a catalyst, comprising:
    mixing a catalytically active component and a surfactant to form a mixture, wherein the catalytically active component comprises phosphorus;
    letting the mixture sit without mixing for greater than 1 hour to form a set mixture;
    subjecting the set mixture to shear to form a sheared mixture;
    combining the sheared mixture with a support; and
    calcining the support with the sheared mixture to form the catalyst.

18. The method of claim 17, wherein the mixture sits until a gel forms.

19. The method of claim 17, wherein the catalyst comprises 0.1 to 20 wt % phosphorus, 0.1 to 75 wt % tin, and 0.1 to 10 wt % of Group 1 and/or 2 metals, based upon a total weight of the catalytically active component.

20. The method of claim 17, wherein the catalyst comprises 0.2 to 25 wt % platinum, 0.2 to 5 wt % tin, 1 to 3 wt % phosphorus, 0.1 to 5 wt % calcium, 0.1 to 2 wt % chlorine, and 0.1 to 4 wt % nickel, based upon a total weight of the catalyst.

* * * * *